(12) United States Patent
Xu et al.

(10) Patent No.: US 11,007,207 B2
(45) Date of Patent: May 18, 2021

(54) PREPARATIONS OF GOLD/MESOPOROUS SILICA HYBRID NANOPARTICLE AND APPLICATIONS

(71) Applicant: University of South Carolina, Columbia, SC (US)

(72) Inventors: Peisheng Xu, Columbia, SC (US); Bei Cheng, Columbia, SC (US); Huacheng He, Columbia, SC (US)

(73) Assignee: University of South Carolina, Columbia, SC (US)

( * ) Notice: Subject to any disclaimer, the term of this patent is extended or adjusted under 35 U.S.C. 154(b) by 82 days.

(21) Appl. No.: 14/833,711

(22) Filed: Aug. 24, 2015

(65) Prior Publication Data
US 2016/0067354 A1  Mar. 10, 2016

Related U.S. Application Data

(60) Provisional application No. 62/070,580, filed on Aug. 29, 2014.

(51) Int. Cl.
| | | |
|---|---|---|
| *A61K 31/704* | (2006.01) | |
| *A61K 41/00* | (2020.01) | |
| *A61K 51/04* | (2006.01) | |
| *B82B 1/00* | (2006.01) | |
| *A61K 51/12* | (2006.01) | |
| *G01N 1/00* | (2006.01) | |
| *A61K 9/51* | (2006.01) | |

(52) U.S. Cl.
CPC ........ *A61K 31/704* (2013.01); *A61K 41/0052* (2013.01); *A61K 51/0482* (2013.01); *A61K 51/1251* (2013.01); *B82B 1/00* (2013.01); *G01N 1/00* (2013.01); *A61K 9/5115* (2013.01)

(58) Field of Classification Search
None
See application file for complete search history.

(56) References Cited

U.S. PATENT DOCUMENTS

| | | | | |
|---|---|---|---|---|
| 8,647,644 | B1* | 2/2014 | Torney ................ | A61K 9/5115 424/400 |
| 2005/0037374 | A1* | 2/2005 | Melker .................... | A61B 5/00 435/6.14 |
| 2010/0016783 | A1* | 1/2010 | Bourke, Jr. ........ | A61K 41/0057 604/20 |
| 2011/0129537 | A1* | 6/2011 | Vo-Dinh ............ | A61K 41/0066 424/490 |

OTHER PUBLICATIONS

Westcott et al. (1998) Langmuir 14(19): 5396-5401.*
Probst et al. (2013) Adv Drug Deliv Rev 65(5): 703-718 (published online Sep. 20, 2012) (Year: 2013).*
Walling et al. (2009) Int J Mol Sci 10: 441-491 (Year: 2009).*
Sun et al. (2011) J. Am. Chem. Soc. 133(46): 18554-18557 (Year: 2011).*
Besson et al. (2009) J/. Materials Chem. 19(27): 4746-4752 (Year: 2009).*
He, Qianjun, and Jianlin Shi. "Mesoporous silica nanoparticle based nano drug delivery systems: synthesis, controlled drug release and delivery, pharmacokinetics and biocompatibility." Journal of Materials Chemistry 21.16 (2011): 5845-5855. (Year: 2011).*
Zhang, Zhenjiang, et al. "Mesoporous silica-coated gold nanorods as a light-mediated multifunctional theranostic platform for cancer treatment." Advanced materials 24.11 (2012): 1418-1423. (Year: 2012).*
Sun, Xiaoxing, et al. "Luciferase and luciferin co-immobilized mesoporous silica nanoparticle materials for intracellular biocatalysis." Journal of the American Chemical Society 133.46 (2011): 18554-18557. (Year: 2011).*
Yuan, et al.; "Facile Synthesis of Highly Biocompatible Poly (2-methacryloyloxy)ethyl phosphorylcholine)-Coated Gold nanoparticles in Aqueous Solution," *Langmuir: the Am. Chem. Soc. J. of Surfaces and Colloids*; 2006, 22, (26), 11022-11027.
Leff, et al., "Synthesis and Characterization of Hydrophobic, Organically-Soluble Gold Nanocrystals Functionalized with Prmary Amines," *Langmuir: the Am. Chem. Soc. J. of Surfaces and Colloids*; 1996, 12, (20), 4723-4730.
Turkevich, et al.; "A Study of the Nucleation and Growth Processes in the Synthesis of Colloidal Gold," *Discussions of the Faraday Society*, 1951, 11, (0), 55-75.
Brust, et al.; "Synthesis of Thiol-derivatised Gold nanoparticles in a Two-phase Liquid-Liquid System," *J. Chem. Soc., Chemical Communications*, 1994, (7), 801-802.
Khan, et al.; "Gold nanoparticles: A paradigm shift in biomedical applications," *Advances in Colloid and Interface Science*; 2013, 199-200, (0), 44-58.
Chang, et al.; "The Shape Transition of Gold Nanorods," *Langmuir : the Am. Chem. Soc. J. of Surfaces and Colloids*; 1998, 15, (3), 701-709.
Van der Zande, et al.; "Aqueous Gold Sols of Rod-Shaped Particles," *The J. Phys. Chem. B*; 1997, 101, (6), 852-854.
Murphy, et al.; "Controlling the Aspect Ratio of Inorganic Nanorods and Nanowires," *Advanced Materials*; 2002, 14, (1), 80-82.
Alkilany, et al.; "Homing Peptide-Conjugated Gold Nanorods: The Effect of Amino Acid Sequence Display on Nanorod Uptake and Cellular Proliferation," *J. Bioconjuate Chem.*; 2014, 25, (6), 1162-71.
Boulos, et al.; "The Gold Nanorod-Biology Interface: From Proteins to Cells to Tissue," *J. Current Physical Chemistry*; 2013, 3, (2).
Sivapalan, et al.; "Off-Resonance Surface-Enhanced Raman Spectroscopy from Gold Nanorod Suspensions as a Function of Aspect Ratio: Not What We Thought," *J. Am. Chem. Soc. Nano*; 2013, 7, (3), 2099-105.
Alkilany, et al.; "Cellular uptake and Cytotoxicity of Gold Nanorods: Molecular Origin of Cytotoxicity and Surface Effects," *Small*, 2009, 5, (6), 701-8.

(Continued)

*Primary Examiner* — Robert J Yamasaki
(74) *Attorney, Agent, or Firm* — Dority & Manning, P.A.

(57) ABSTRACT

Described is a method to fabricate a gold/mesoporous silica hybrid nanoparticle. According to the process, a gold nanoparticle can be conjugated onto the surface of a mesoporous silica nanoparticle to yield a photothermal stable theranostic platform, gold/mesoporous silica hybrid nanoparticle. The nanoparticles can be useful for disease detection, treatment, and monitoring.

19 Claims, 9 Drawing Sheets

(56) References Cited

OTHER PUBLICATIONS

Norman, et al.; Targeted Photothermal Lysis of the Pathogenic Bacteria, *Pseudomonas aeruginosa*, with Gold Nanorods, *Nano Lett.*; 2008, 8, (1), 302-6.
Orendorff, et al.; "Aspect ratio dependence on surface enhanced Raman scattering using silver and gold nanorod substrates," *J. Physical Chemistry Chemical Physics: PCCP*; 2006, 8, (1), 165-70.
Gole, et al.; "Immobilization of Gold Nanorods onto Acid-Terminated Self-Assembled Monolayers via Electrostatic Interactions," *Langmuir: the Am. Chem. Soc. J. ofSurfaces and Colloids*; 2004, 20, (17), 7117-22.
Dreaden, et al., "Small Molecule-Gold Nanorod Conjugates Selectively Target and Induce macrophage Cytotoxicity towards Brest Cancer Cells," *Small*, 2012, 8, (18), 2819-22.
Tabor, et al, "Effect of Orientation on Plasmonic Coupling between Gold Nanorods," *Am. Chem. Soc. Nano*, 2009, 3, (11), 3670-8.
Lee, et al.; "Gold and Silver Nanoparticles in Sensing and Imaging: Sensitivity of Plasmon Response to Size, Shape, and Metal Composition," *Am. J. Phys. Chem. B*; 2006, 110, (39), 19220-5.
Jain, et al.; "Plasmon Coupling in Nanorod Assemblies: Optical Absorption, Discrete Dipole Approximation Simulation, and Exciton-Coupling Model," *Am. J. Phys. Chem. B*; 2006, 110, (37), 18243-53.
Eustis, et al.; "Aspect Ratio Dependence of the Enhanced Flourescence Intensity of Gold Nanorods: Experimental and Simulation Study," *J. Phys. Chem. B*; 2005, 109, (34), 16350-6.
Sun, et al.; "Using SV119-Gold Nanocage Conjugates to Eradicate Cancer Stem Cells through a Combination of Photothermal and Chemo Therapies," *Adv. Health Mater*; Aug. 2014, 3(8); pp. 1283-1291.
Wang, et al.; "SV119-Gold nanocage conjugates: a new platform for targetiang cancer cells via sigma-2 receptors," *Nanoscale*; 2012, 4, (2), pp. 421-424.
Xia, et al.; "An enzyme-sensitive probe for photoacoustic imaging and fluorescence detection of protease activity," *Nanoscale*; 2011, 3, (3), 950-3.
Yavuz, et al.; "Gold nanocages covered by smart polymers for controlled release with near-infrared light," *Nature Materials*; 2009, 8, (12), 935-9.
Skrabalak, et al.; "Facile synthesis of Ag nanocubes and Au nanocages," *Nature Protocols*; 2007, 2, (9), 2182-90.
Cang, et al.; "Gold nanocages as contrast agents for spectroscopic optical coherence tomography," *Optics Letters*; 2005, 30, (22), 3048-50.
Prigodich, et al.; "Multiplexed Nanoflares: mRNA Detectionin Live Cells," *Analytical Chemistry*; 2012, 84, (4), 2062-6.
Prigodich, et al.; "Nano-flares for mRNA Regulation and Detection," *Am. Chem. Soc. Nano*; 2009, 3, (8), 2147-52.
Cheng, et al.; "Deep Penetration of a PDT Drug into Tumors by Noncovalent Drug-Gold Nanoparticle Conjugates," *J. Am. Chem. Soc.*; 2011, 133, (8), 2583-91.
Jana, et al.; "Wet Chemical Synthesis of High Aspect Ratio Cylindrical Gold Nanorods," *J. Phys. Chem. B*; 2001, 105, (19), 4065-4067.
Jana, et al.; "Seed-Mediated Growth approach for Shape-Controlled Synthesis of Spheroidal and Rod-like Gold Nanoparticles Using a Surfactant Template," *Advanced Materials*; 2001, 13, (18), 1389-1393.
Nikoobakhi, et al.; "Preparation and Growth Mechanism of Gold Nanorods (RNs) Using Seed-Mediated Growth Method," *Chem. Mater.*; 2003, 15, (10), 1957-1962.
Austin, et al.; "The optical, photothermal, and facile surface chemical properties of gold and silver nanoparticles in biodiagnostics, therapy, and drug delivery," *Arch. Toxicol.*; 2014, 88, (7), 1391-417.
Dickerson, et al.; "Gold nanorod assisted near-infrared plasmonic photothermal therapy (PPTT) of squamous cell carcinoma in mice," *Cancer Letters*; 2008, 269, (1), 57-66.
Mackey, et al.; "The Most Effective Gold nanorod Size for Plasmonic Photothermal Therapy: Theory and In Vitro Experiments," *J. Phys. Chem. B*; 2014, 118, (5), 1319-26.
Link, et al.; "Laser-Induced Shape Changes of Colloidal Gold Nanorods Using Femtosecond and Nanosecond Laser Pulses," *J. Phys. Chem. B*; 2000, 104, (26), 6152-6163.
Chen, et al.; Gold Nanocages: Engineering Their Structure for Biomedical Applications, *Advanced Materials*; 2005, 17, (18), 2255-2261.

* cited by examiner

PREPARATIONS OF GOLD/MESOPOROUS SILICA HYBRID NANOPARTICLE AND APPLICATIONS

CROSS REFERENCE TO RELATED APPLICATION

This application claims filing benefit of U.S. Provisional Application Ser. No. 62/070,580 having a filing date of Aug. 29, 2014, which is incorporated herein by reference in its entirety.

BACKGROUND

Various types of gold nanoparticles, including gold nanospheres, gold nanorods, and gold nanocages have been studied extensively in biomedical applications such as drug and gene delivery, biosensing, disease detection, disease treatment, and response monitoring due to their good biocompatibility. For instance, gold nanoparticles have been used as diagnostic tools for various diseases, including cancers, heart and vascular diseases, central nervous system diseases, rheumatoid arthritis, etc. Because of the localized surface plasmon resonance and surface-enhanced Raman scattering effects, gold nanoparticles have also been widely used in the field of biosensing and imaging.

Gold nanoparticles have been extensively explored for use in photothermal therapy due to their light/heat converting capacity in the near infrared (NIR) window. Upon irradiation, gold nanoparticles generate heat attributable to the localized surface plasmon resonance phenomenon. By manipulating their shape, size, and geometry, the surface plasmon resonance peak of gold nanorods, gold nanospheres, and gold nanocages can be tuned to the NIR region (650-900 nm), also called the tissue transparent window, within which light can penetrate deeply into tissue. Upon NIR irradiation, properly tuned gold nanoparticles generate heat and thus it is expected that they can be utilized for localized photothermal therapy.

Although gold nanoparticles have been evaluated in numerous systems and proven to be promising in both photothermal therapy and drug delivery, there are several intrinsic properties limiting their translation from bench to clinical practice. Due to their poor photothermal stability, traditional gold nanoparticles gradually lose their photothermal converting capacity upon repetitive NIR irradiation. It has been well documented that the shape and extinction of gold nanorods change after NIR laser irradiation resulting in lower heat generating capacity after each heating/cooling cycle. Similar scenarios also have been observed in gold nanospheres and gold nanocages if the generated heat is not adequately dissipated to the surrounding environment. Moreover, without suitable heat dissipation, gold nanocages can melt to form gold nanospheres.

Gold nanoparticle-based drug delivery systems have also been developed but with limited success. For instance, benefiting from its empty core, various functionalized gold nanocages have been investigated for drug delivery. Unfortunately, except for gold nanocages, gold nanoparticles are not good drug carriers either due to limited drug loading capacity or poorly controlled drug release profile. Moreover, as mentioned above, gold nanocages can melt to form gold nanospheres under photothermal therapy conditions. Thus, while tremendous efforts have been devoted to the effort, methods to effectively integrate both photothermal therapy and chemotherapy modules into one gold nanoparticle based system remains a challenge, especially when repetitive activation is desired.

Similar to examination of gold nanoparticles, increasing attention has been gained by mesoporous silica nanoparticles for use in biological application due to the high and versatile drug loading capacity as well as good biocompatibility. Numerous mesoporous silica nanoparticle based carrier systems have been developed for the delivery of drugs, peptides, DNAs, and siRNAs. To better control the release kinetics of their payloads, many control factors have been explored for use in conjunction with the mesoporous silica nanoparticles, such as polyelectrolytes, macrocyclic organic molecules, and inorganic nanoparticles.

Unfortunately, these delivery systems have been shown to be responsive to changes in the physiological environment, such as pH and redox potential. Thus, once the nanoparticle is administrated in vivo, the drug release profile will be out of the control of the clinician and will be due only to the fabrication method and biodistribution.

Methods and materials that can integrate both photothermal therapy and chemotherapy modules into one system remains a challenge, especially when repeated activation is needed. Development of such methods and materials would be of great benefit.

SUMMARY

According to one embodiment, disclosed are hybrid nanoparticles that include a mesoporous silica nanoparticle and a plurality of gold nanospheres bonded to the mesoporous silica nanoparticle through the linkage of disulfide bonds.

Also disclosed are methods for forming the hybrid nanoparticles. For instance, a method can include functionalizing a mesoporous silica nanoparticle with a first reactivity (e.g., thiol), functionalizing a plurality of gold nanospheres with a second reactivity (e.g., thiol), and reacting the two together such that the plurality of gold nanospheres are bonded to a surface of the mesoporous silica nanoparticle.

A method for photothermally treating a living cell by use of the hybrid nanoparticles is also disclosed. For instance, a method can include locating a hybrid nanoparticle in an environment, the environment comprising a living cell, and directing near infrared (NIR) radiation at the hybrid nanoparticle (e.g., from 650 nanometers to 900 nanometers). The interaction between the hybrid nanoparticles and the NIR increases the temperature in the environment, which can lead to cell destruction. Beneficially, the hybrid nanoparticles can retain photothermal effects over multiple repetitions of the photothermal process.

BRIEF DESCRIPTION OF THE FIGURES

A full and enabling disclosure of the present invention, including the best mode thereof, directed to one of ordinary skill in the art, is set forth in the specification, which makes reference to the appended figures, in which.

Figure 1:
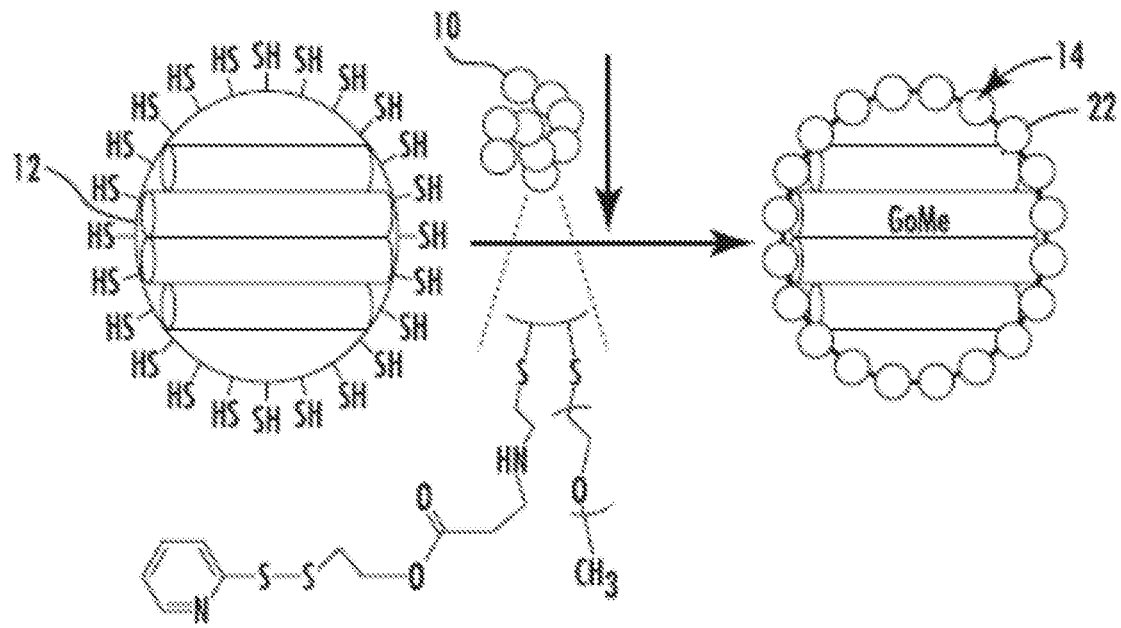
FIG. 1 schematically illustrates a fabrication method for gold/mesoporous silica nanoparticles (GoMe) from mesoporous nanoparticles (MSN) and PEGylated gold nanospheres (PEG-GNS) surface functionalized with 2-(pyridin-2-yldisulfanyl)ethyl acrylate (PDA-GNS) via thiol-disulfide exchange reaction.

Repeat use of reference characters throughout the present specification and appended drawings is intended to represent same or analogous features or elements of the invention.

DETAILED DESCRIPTION

The following description and other modifications and variations to the presently disclosed subject matter may be practiced by those of ordinary skill in the art, without departing from the spirit and scope of the present disclosure. In addition, it should be understood that aspects of various embodiments may be interchanged both in whole and in part. Furthermore, those of ordinary skill in the art will appreciate that the following description is by way of example only, and is not intended to limit the disclosed subject matter.

The present disclosure is generally directed to a gold/mesoporous silica hybrid nanoparticle-based therapeutic/diagnostic platform that can be utilized for disease detection, drug delivery, photothermal therapy, and other biomedical applications. More specifically, disclosed are gold/mesoporous silica hybrid nanoparticles and methods of forming the nanoparticles. Beneficially, the disclosed nanoparticles can be extremely stable upon repetitive NIR irradiation. Furthermore, the nanoparticles can be effectively utilized for drug delivery, with release of the payloads from the nanoparticles remotely controlled in one embodiment by NIR irradiation. The gold/mesoporous silica hybrid nanoparticles can be beneficially utilized in a wide variety of biomedical applications including, but not limited to, drug delivery, gene delivery, photothermal therapy, and disease diagnostics.

According to the present disclosure, gold nanosphere/mesoporous silica hybrid nanoparticles can be formed by conjugating gold nanospheres onto the surface of mesoporous silica nanoparticles. Beneficially, the photothermal properties of the hybrid nanoparticles can remain intact after multiple heating/cooling cycles induced by NIR light irradiation. Furthermore, the nanoparticles can be utilized in drug delivery, and release of the payload from the hybrid nanoparticles can be triggered through NIR irradiation. As such, the gold/mesoporous silica hybrid nanoparticles can serve as a repeatedly activatable carrier for remote controlled delivery of biologically active agents (e.g., drugs, genetic transformation vectors, etc.) through the combination of the best characteristics of both conventional gold nanoparticles and mesoporous silica nanoparticles. The hybrid nanoparticles can display excellent photothermal converting ability as well as high drug loading capacity and triggerable drug release.

In contrast to gold nanorods and other heat generating gold nanoparticles that have been examined in isolation, the hybrid nanoparticles are photothermally stable and can be repetitively activated through NIR irradiation. The nanoparticles can be utilized in both drug delivery, detection, and other biomedical applications. For instance, hybrid nanoparticles loaded with a chemotherapy agent such as doxorubicin (DOX@GoMe) can be sensitive to both NIR irradiation and intracellularly elevated redox potential. Thus, chemotherapy loaded hybrid nanoparticles coupled with NIR irradiation can exhibit a synergistic effect of both photothermal therapy and chemotherapy in killing cancer cells.

The hybrid nanoparticles can also be utilized in detection. For instance, the hybrid nanoparticles can be labeled with a detectable substance, e.g., $^{64}Cu$. The labeled hybrid nanoparticles can be used to successfully detect the existence of clinically relevant targets, e.g., spontaneous lung tumors through PET imaging.

FIG. 1 illustrates one scheme for the fabrication of the hybrid nanoparticles from mesoporous silica nanoparticles and functionalized gold nanospheres through a thiol-disulfide exchange reaction. Specifically, gold nanospheres 10 can be grafted onto the surface of a mesoporous silica nanoparticle 12 through disulfide bonds, which can endow the hybrid nanoparticles with intracellular redox potential responsiveness.

Gold nanoparticles suitable for use in forming the hybrid nanoparticles generally include about 50% or more gold by weight, for instance about 60%, about 70%, about 80% or about 90% or more gold by weight. In one embodiment, a gold nanoparticle can be formed essentially completely of gold atoms. In general, the gold nanoparticles can be substantially spherical in shape, i.e., gold nanospheres, but this is not a requirement of the disclosure and the gold nanospheres need not be perfectly spherical.

Formation processes used to form the gold nanoparticles are not particularly limited. Typical formation processes for the gold nanoparticles can include the reduction of a metal salt precursor solution in the presence of a stabilizing reagent. This is typically accomplished by using an aqueous solution of an acid and gold chloride, in which the acid acts as both reducing agent and stabilizing reagent for the formed gold nanoparticles. Reducing agents and solvents as are known in the art can be utilized. For example, the gold nanoparticles can be formed by reducing a gold salt (e.g., chloride (III) trihydrate) with a suitable reducing agent, e.g., citric acid, acetic acid, etc.

The average size and distribution of the particles can be controlled as is known by varying the concentration of the metal precursor, the type and concentration of the reducing agent, the temperature of the growth phase, and the time of the growth phase. The diameter of the gold nanoparticles is not particularly limited, and can be in one embodiment from about 1 nanometer to about 100 nanometers, from about 2 nanometer to about 50 nanometers, or from about 5 nanometers to about 40 nanometers in some embodiments.

Mesoporous silica nanoparticles for use in forming the hybrid nanoparticles generally include a silica body defining a plurality of pores therein. The silica body is not limited to only silica in the structure, and may include materials other than silica incorporated within the body, though the body can generally be formed of a majority of silica, e.g., about 60% or more, about 70% or more, about 90% or more, or about 95% or more by weight silica in some embodiments. In some embodiments, the mesoporous silica nanoparticles may be substantially spherical with a plurality of pore openings through the surface providing access to the pores. However, the mesoporous silica nanoparticles can have shapes other than substantially spherical shapes in some embodiments. In general, the mesoporous silica nanoparticles can have a diameter of about 10 nanometers or greater, for instance about 20 nanometers or greater, for instance from about 10 nanometers to about 200 nanometers in largest cross sectional dimension, or from about 20 to about 100 nanometers in largest cross sectional dimension in some embodiments.

Generally, the mesoporous silica nanoparticles define an outer surface between the pore openings, as well as side walls within the pores. The pores can extend through the body to another pore opening, or can extend only partially through the silica body such that a pore can have a closed end surface within the body that is defined by the silica body.

As utilized herein, "mesoporous" generally refers to pores having a cross sectional dimension (e.g., diameter) between about 2 nanometers and about 50 nanometers. The mesoporous silica nanoparticles can include an amount of pores that are larger (macroporous) and/or smaller than the mesopores (microporous) in addition to the mesopores. As utilized herein, "microporous" generally refers to pores with a diameter smaller than about 2 nanometers and "macroporous generally refers to pores with a cross sectional dimension greater than about 50 nanometers.

In one embodiment, the pores of the mesoporous silica nanoparticles can be large enough to contain one or more compounds therein for delivery by use of the hybrid nanoparticles. In such embodiments, the pores can allow molecules, for example, drugs including therapeutic compound such as anticancer compounds, to temporarily adhere or bind to the inside surface of the pores, and to be released from the hybrid nanoparticles when used for therapeutic purposes. Other agents as may be incorporated within or on the mesoporous silica nanoparticles either alone or in conjunction with another active agent such as a drug can include photosensitizers. A photosensitizer can meet the following conditions: (1) maximum absorption wavelength between 600-800 nm, and limited absorption between 400-600 nm; (2) high singlet oxygen yield; (3) strong phototoxicity and weak dark toxicity; (4) high retention ratio in malignant tumor tissues; (5) single component; and (6) fluorescence. A photosensitizer as can be incorporated in a hybrid nanoparticle can include, without limitation, haematoporphyrins, phthalocyanine, chlorophylls, porphin or their derivatives such as acidified porphyrin, hemoporphyrin and their derivatives thereof, or the metal ion-complex of phthalocyanine and derivatives thereof, and so forth.

The pore sizes of the mesoporous silica nanoparticles can be controlled according to standard practice. For instance, variation and control of pore sizes may be carried out by use of different surfactants or swelling agents during the preparation of the silica nanoparticles.

Referring again to FIG. 1, the surface-assembled gold nanospheres 22 on the hybrid nanoparticle 14 can be considered structurally as a well-defined assembly of "chainlike gold nanoparticles" or a discontinuous configuration of gold nanospheres, either of which being capable of efficiently generating heat upon NIR irradiation.

The term nanoparticles as used herein is intended the include particles as large as about 1000 nm. For instance, the hybrid nanoparticles can have a largest cross sectional dimension (e.g., diameter) of about 30 nanometers or larger, about 50 nanometers or larger, or about 100 nanometers or larger in some embodiments, as measured by transmission electron microscopy (TEM) or similar visualization technique. Particle size does not refer to agglomerates in solution or suspension.

Without wishing to be bound to any particular theory, it is believed that the hybrid nanoparticles are able to maintain the original shape after NIR irradiation due to the distance between each individual gold nanosphere that is maintained on the supporting mesoporous silica nanoparticle. Consequently, the hybrid nanoparticles can exhibit stable photothermal properties. In addition, because the release kinetics of the hybrid nanoparticles are sensitive to NIR irradiation, drug loaded hybrid nanoparticles can exhibit a synergistic effect in drug delivery and photothermal treatment, e.g., in destruction of cancer cells.

As described further herein, the hybrid nanoparticles can be formed by initial functionalization of gold nanospheres with PDA. Due to the abundance of PDA segments on the gold nanospheres, an excess of the PDA can remain on the hybrid nanoparticles following conjugation of the PDA functionalized gold nanospheres with the mesoporous silica nanoparticles. As such, the hybrid nanoparticles can be further functionalized. By way of example, the excess PDA of the hybrid nanoparticles can be utilized to modify the hybrid nanoparticles with DOTA to achieve excellent chelating capacity, for instance as may be utilized for PET imaging.

Targeting ligands can be incorporated on the hybrid nanoparticles in some embodiments. For example, the gold/mesoporous silica hybrid system can be capable of detecting clinically relevant spontaneous tumors by use of a targeting ligand following which the hybrid nanoparticles can provide the synergetic effect of photothermal therapy and chemotherapy in killing the detected cancer cells. By way of example, tumor targeting ligands, such as RGD peptide, folic acid, and anisamide, which target cancer cells overexpressed integrins, folate, and sigma-2 receptors, respectively, can be ligated to the hybrid nanoparticles.

In contrast to previously known mesoporous silica nanoparticle based systems, the hybrid nanoparticles can be well dispersed in a serum-containing medium. In addition, and contrary to gold nanorods and other heat generating gold nanoparticles that have been used in isolation, the disclosed hybrid nanoparticles are stable in structure and maintain the photothermal converting capacity after repetitive NIR irradiation.

The release of a bioactive agent from the hybrid nanoparticles can be triggered by intracellular elevated redox potential as well as by NIR irradiation, which can improve control of drug delivery by use of the hybrid nanoparticles.

Due to the presence of the gold nanoparticles on the hybrids, the localization of the hybrid nanoparticles (e.g., drug loaded hybrid nanoparticles) can be detected by both fluorescence and dark-field microscopies for improved targeting of drugs by use of the materials. In addition, the integration of photothermal therapy and chemotherapy in the single hybrid system can improve therapies through a synergistic effect. Furthermore, the hybrid nanoparticles are an excellent tool for imaging processes (e.g., PET imaging) and can be utilized in one embodiment in the detection of tumors, e.g., clinically relevant spontaneous lung tumor. Based on the promising in vitro and in vivo results presented in more detail below, the hybrid nanoparticles can be beneficially utilized in one embodiment as an effective tool for image-guided cancer therapy.

EXAMPLE

Materials

Terraethylorthosilicate (TEOS), (3-Mercaptopropyl) trimethoxysilan) (MPTMS), hexadecyltrimethyl ammonium bromide (CTAB), sodium hydroxide (NaOH), Pluronic® F-127, ammonium nitrate, methanol, gold chloride trihydrate, cysteamine hydrochloride, 2,2'-dipyridyl disulfide, triethylamine (TEA), Doxorubicin (DOX), and sodium borohydride ($NaBH_4$) were purchased from Sigma-Aldrich. PEG2000-SH was purchased from Laysan Bio. Ethanol and acetic acid were acquired from Fisher Scientific.

Synthesis of Mesoporous Silica Nanoparticles (MSN)

The MSN was synthesized in a dual surfactant system using a classic fast self-assembling method containing both the cationic surfactant cetyl trimethylammonium bromide (CTAB) and non-ionic surfactant triblock polymer Pluronic® F-127 to obtain a good suspending nano-sized MSN. In a typical synthesis, CTAB (50 mg) and Pluronic® F-127 (40 mg) were dissolved in 24 mL DI water. Following, NaOH aqueous solution (175 µL, 2M) was added into the above mixture. The reactants were heated to 80° C. with vigorous stirring for 30 min. TEOS (200 µL) was added dropwise to the above solution followed by 3-Mercaptopropyl trimethoxysilan (MPTMS, 20 µL). A white precipitant was formed after a few minutes and the mixtures were allowed to stir for 2 h at 80° C. The crude product was collected by centrifugation at 16,000 rcf for 15 min. CTAB was removed through ion exchange by washing in ethanol solution of $NH_4NO_3$ at 50° C. This process was repeated 3 times, followed by extensive washing with ethanol and the purified product was stored at 4° C. in ethanol solution.

Synthesis of PEG Stabilized Gold Nanosphere (PEG-GNS)

Super-stable gold nanospheres were synthesized according to the literature with minor modification. Briefly, gold (III) chloride trihydrate (12 mg) was first dissolved in 18 mL isopropyl alcohol and followed by the addition of 0.2 mL acetic acid. Thiolated polyethylene glycol (PEG-SH, MW=2000 Da) (15.24 mg in 2 mL isopropyl alcohol) was added into the gold alcohol solution. The mixture was stirred for 1 h at room temperature following the addition of sodium borohydride (37.84 mg in 1.5 mL methanol). The reaction mixture was stirred vigorously overnight at room temperature. After overnight reaction, the mixture was centrifuged for 30 min (2500 rcf) to remove large particles. The resulting supernatant was precipitated in hexane. The precipitant was re-dispersed in 5 mL DI water. To remove free PEG-SH from the gold nanoparticles, the PEG-GNS was purified by repeatedly washing with water in a Millipore Centricon (MWCO=10,000 Da).

Figure 2A:
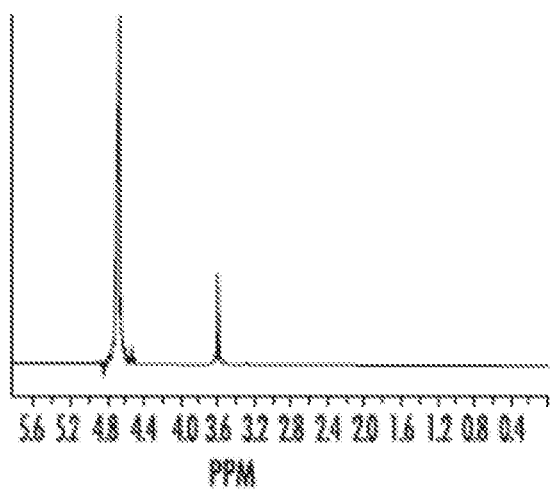
FIG. 2A includes $^1$H-NMR of PEG-GNS in $D_2O$.

The successful anchoring of PEG-SH onto the gold nanospheres was confirmed by $^1$H-NMR (FIG. 2A). The zeta potential of the PEG-ylated gold nanospheres (PEG-GNS) was measured by Zetasizer Nano ZS (Malvern) and showed a near neutral potential (−8.65 mV), which further confirmed the successful coating of PEG onto the gold nanospheres. The morphology of PEG-GNS was confirmed by TEM. The UV-Vis spectrum of PEG-GNS was recorded by UV-Vis spectrophotometer (DU® 650 Spectrophotometer, Beckman Coulter, USA), which showed an absorbance peak at 510 nm.

Synthesis of 2-(pyridin-2-yldisulfanyl)ethyl Acrylate Modified Gold Nanospheres (PDA-GNS)

Figure 2B:
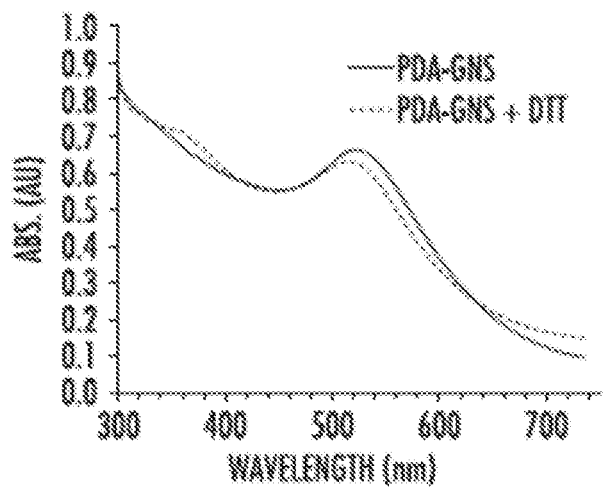
FIG. 2B includes the UV-Vis spectra of PDA-GNS.

PDA-GNS was synthesized in a two-step procedure by conjugating PEG-GNS with cysteamine first, followed by reacting with 2-(pyridin-2-yldisulfanyl)ethyl acrylate (PDA) through Michael addition reaction. Briefly, the PEG-GNS synthesized above was dispersed in 10 mL DI water, and then cysteamine (0.216 mg in 40 μL $H_2O$) was added. The mixture was kept stirring at room temperature. After 24 h of stirring, the reaction solution was loaded to a Millipore Centricon® (MWCO=10,000 Da) and repeatedly washed by centrifugation to remove un-reacted cysteamine. The successful conjugating of cysteamine was confirmed by zeta potential measurement, which showed a highly positive charge (+27 mV) on the nanosphere surface. The surface amine concentration was further measured by TNBSA assay, which also proved the successful replacement of PEG by cysteamine. The gold nanosphere concentration was determined by calculating UV-Vis absorbance according to literature. The result showed that there were around 1000 —$NH_2$ groups located on the surface of each nanosphere. After that, PDA was conjugated to the gold nanospheres by reacting with amine groups via Michael addition reaction. Typically, cysteamine modified gold nanospheres were dispersed in 500 μL of DMSO, and triethylamine (0.265 μL in 26.5 μL DMSO) was added, following the addition of PDA (0.459 mg in 50 μL DMSO). The ratio between —$NH_2$ and PDA was optimized at 2:1 since a higher —$NH_2$ to PDA ratio could easily result in nanosphere aggregation during the post-purification process. The reaction mixture was purged with nitrogen and then kept at 50° C. for 24 h. The resulting PDA-GNS was precipitated in cold ether for three times to remove unreacted PDA and finally re-dispersed in 2 mL DI water. The successful conjugation of PDA was confirmed by UV-Vis spectrum (FIG. 2B). PDA-GNS showed a PDA characteristic peak around 375 nm after reacting with dithiothreitol (DTT). The PDA concentration of PDA-GNS was measured by DTNB assay, which proved that about 200 molecules of PDA was anchored to each gold nanosphere.

Encapsulation of Doxorubicin (DOX) into Mesoporous Silica Nanoparticles (MSN)

To load DOX into MSN, DOX.HCl was firstly converted to its base form by mixing with triethylamine for 30 min. In a typical synthesis batch, 10 mg DOX was added to 18.6 mg MSN and the mixture was sonicated for 30 min to obtain a uniform dispersion. The mixture was stirred at room temperature for 24 h and the unloaded DOX was removed by washing with DI water twice. The loaded nanoparticles were denoted as DOX@MSN. The loading efficiency of DOX was quantified by a fluorospectrometer (Beckman Coulter, DTX 880). Different loading of DOX can be simply tuned by changing the ratio between DOX and MSN. In this experiment, the highest drug loading content of DOX in DOX@MSN reached 28%.

Fabrication of Gold Nanosphere Decorated Mesoporous Silica Nanoparticles (GoMe)

Gold nanospheres were grafted onto mesoporous silica nanoparticles through thiol-disulfide exchange reaction. MSN (200 μg in 200 μL) aqueous solution was added to 2 mL PDA-GNS aqueous suspension while stirring. The mixture was allowed to react at room temperature for 24 h, and then washed three times with DI water. The final product was collected by centrifugation. The size and morphology of the hybrid nanoparticles (GoMe) was determined by TEM.

Photothermal Stability Assay

Repetitive laser irradiation experiments were carried out to test the photothermal stability of GoMe and gold-nanorod. Firstly, the concentration of GoMe and gold nanorod were adjusted to generate equal increment in temperature upon the same intensity of laser irradiation. The GoMe suspension was irradiated by an 808 nm laser for 10 min (Scorpius D-700 laser, 2.83 W/cm$^2$). The temperature of the nano-suspension was monitored with a FLIR i7 thermal imaging camera and recorded every 30 sec. Both the GoMe and the gold nanorod (maximum absorbance peak at 804 nm) underwent 6 continuous laser irradiation cycles (10 min irradiation and 20 min cooling). The 7$^{th}$ irradiation was applied 24 h after the 6$^{th}$ cycle. The UV-vis spectra and TEM images were recorded to reveal the change during the repeating cycles. The photothermal stability of GoMe in reducing environment was further investigated by dispersing GoMe in DI water supplemented with 10 mM glutathione.

Laser Irradiation Triggered Release of GoMe

To evaluate the responsiveness of GoMe to NIR light, 20 μL of GoMe containing 4 μg of DOX was diluted with 250 μL DI water. The GoMe suspension was incubated at 37° C. to carry out the release study. GoMe nano-suspension was centrifuged at 1, 2, 4, 6, 8, 12, and 24 h at 16,000 rcf for 10 min to separate released DOX from GoMe particles. Following, the same amount of fresh medium was added to resuspend the GoMe pellet. At 24 h post the start of the releasing experiment, the GoMe suspension was irradiated by a 808 nm laser for 10 min (2.83 W/cm$^2$). Sample was collected immediately by centrifugation after the irradiation. The sample was then incubated at 37° C. followed by sampling twice (at 1 h intervals), and then incubated till the next 24 h point. The whole release process was continued for 4 days. The amount of DOX in the supernatant was determined by a fluorospectrometer (Beckman Coulter DTX 880, excitation: 485 nm and emission: 545 nm).

Gold Nanospheres Decorating Density Effect Assay

The effects of different gold nanosphere density on a single mesoporous silica nanoparticle were explored by examining the product of the reaction between gold nanospheres and mesoporous silica nanoparticles at different time intervals. The reaction was carried out in a transparent 2.5 mL spectrophotometer cuvette. The UV absorbance spectrum was recorded directly as the reaction proceeding, while the photothermal converting capacity of the mixture was examined by irradiating the diluted reaction mixture with an 808 nm laser. The reaction was also monitored by observing the morphology of GoMe with the help of TEM.

Cellular Internalization Assay

The A2058 cell, a human melanoma cell line, was cultured in Dulbecco's modification of eagle medium (Corning, Manassas, Va.) supplemented with 10% FBS and 1% penicillin-streptomycin (Life Technology, Grand Island, N.Y.) at 37° C. in 5% humidified $CO_2$ atmosphere. Cells were seeded in 35 mm petri dishes with a density of 200,000 cells/petri dish. After overnight incubation, 5 µM DOX@GoMe was added and continued incubation for another 3 h. Cells were washed once with complete medium and then stained with Hoechst 33342, followed by confocal microscopy imaging (LSM 700, Zeiss) and dark field microscopy imaging (Leica DM6000 M).

Live/Dead Cell Assay after Photothermal Therapy

The photothermal effect of GoMe in cell culture medium was evaluated in a 96-well plate. GoMe of different concentrations were added to each well containing 100 µL complete medium. The resulting GoMe nano-suspension was irradiated with NIR laser (808 nm, 2.83 W/cm$^2$) for 10 min at predesigned time intervals and its temperature was monitored with a FLIR i7 thermal imaging camera and recorded every 1 min. To visualize the effect of laser irradiation on the cell death, Live/Dead cell imaging kit (Molecular Probe®) was used. 10,000 cells were seeded in 96-well plate and incubated at 37° C. in 5% $CO_2$ overnight. Blank GoMe (1 µM or 5 µM) was added and incubated for 2 h. For GoMe treated groups, a 808 nm laser was used to irradiate cells for 10 min, while others had no laser treatment. Cells were kept in the incubator for 2 h and stained with Live/Dead cell imaging kit according to the manufacturer's instruction. Each well was imaged from 5 different positions (top, bottom, left, right and middle) with fluorescent microscopy (Axiovert 200, Carl Zeiss) under 20× magnification using FITC and Texas red channels.

Cytotoxicity Assay

For cell viability assays, A2058 cells were seeded in a 96-well plate (10,000 cells/well) and incubated at 37° C. in 5% $CO_2$ overnight. DOX, MSN, DOX@MSN, GoMe, and DOX@GoMe were diluted with complete medium to achieve targeted concentrations. After 24 h of incubation, GoMe and DOX@GoMe irradiation groups were exposed to 808 nm laser irradiation for 10 min. The cells were allowed to grow overnight and then added with MTT reagent. MTT stop solution was added after 4 h of incubation to dissolve MTT formazan crystals. The optical density of the medium was measured using a microplate reader (ELX808, Bio-Tech Instrument, Inc.) at λ=595 nm.

$^{64}$Cu Radiolabeling of Hybrid Nanoparticles

DOTA was conjugated onto GoMe nanoparticles by adding maleimido-mono-amide-DOTA (20 mM, 50 µL in DMSO) to 1 mg GoMe aqueous solution (1 mg/ml). After 6 h of reaction at room temperature, the free DOTA was separated from GoMe by centrifugation and washing with DI water twice. The resulting pellet was re-suspended in 1 ml DI water. GoMe nanoparticles were further radiolabeled by $^{64}$Cu via the DOTA chelator. The radiolabeling was accomplished by addition of 1.0-1.5 mCi of $^{64}$CuCl$_2$ in 0.1 M HCl (University of Wisconsin) to a mixture of 50 µL 0.1 N ammonium acetate (pH 5.5) buffer and 150-200 µL of the nanoparticles suspension, followed by incubation at 37° C. for 30 min. The radiolabeled nanoparticles were collected into 300-400 µL of phosphate buffered saline by centrifugation.

Animal Model Establishment

Female FVB mice aged 6-8 weeks received weekly intraperitoneal (IP) injections of 1 mg urethane/g body weight dissolved in sterile 0.9% NaCl. Twenty weeks after the initial urethane injection, MRI was used to verify lung tumor presence. PET imaging was performed when at least one lung tumor reached 1.5 mm in diameter.

MRI and PET Animal Imaging

Twenty-four weeks after urethane treatment, lung tumor bearing mice were first imaged on a 7 Tesla ClinScan MRI system (Bruker BioSpin Corporation, Billerica, Mass.), Inc., Palo Alto, Calif.). MRI were acquired with a cardiac and respiratory gated, multi-slice, spin-echo sequence developed with the following parameters: field of view 30 mm, effective matrix=192×192 zero-filled to 256×256, slice thickness 0.7 mm, TR was a function of the breathing cycle and averaged to about 1 second. The TE was 11 ms, the number of averages was 4, the number of slices was 15 with a gap equal to 0.7 mm between slices to avoid crosstalk. The slice stack was moved by 0.7 mm and 15 other interleaved slices were acquired. Gadolinium-DTPA contrast agent (Magnevist; Bayer Schering Pharma, Berlin, Germany) was injected at a dose of 50 mmol/kg body weight in the hind leg muscle. Before PET imaging, mice were injected with $^{64}$Cu-labeled GoMe nanoparticles via the lateral tail vein. Each mouse received 500-750 µCi of $^{64}$Cu for a total volume of 150-200 µL. Mice were imaged using a Focus 120 PET scanner (Positron Emission Tomography) (Siemens, Knoxville, Tenn.) at 6 h and 20 h post administration. During the 40 min PET acquisition, anesthesia was maintained using 1.25% isoflurane in $O_2$ inhaled through a nose cone. Heart rate, respiration, and rectal temperature were monitored (SAII, Stony Brook, NY). PET data were reconstructed using OSEM algorithm with 2 iterations and 12 subsets followed by MAP algorithm (18 iterations). The reconstructed image (not corrected for attenuation) was composed of 95 axial slices of thickness 0.79 mm with an in-plane voxel dimension of 0.4 mm×0.4 mm (128×128 pixels).

Gold/Mesoporous Silica Hybrid Nanoparticle (GoMe) Fabrication

Figure 3:
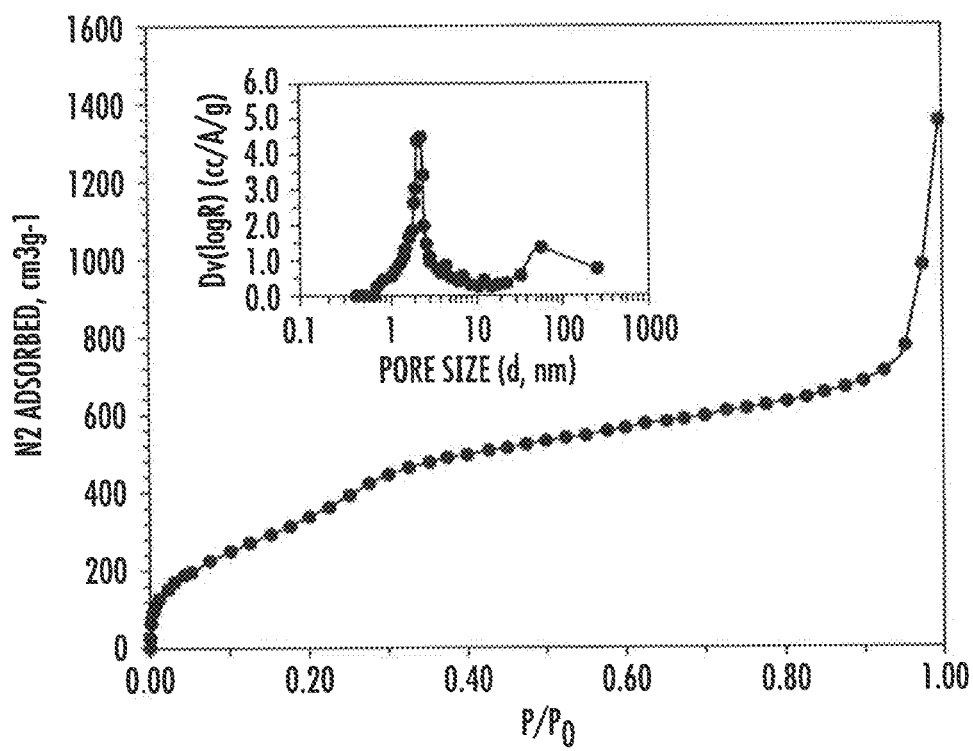
FIG. 3 illustrates the nitrogen sorption isotherm for MSN. The insert shows the pore size distribution.

TEM revealed that most mesoporous silica nanoparticles were in spherical or oval shape with a size (cross sectional dimension) of 50.87±10.69 nm. The $N_2$ sorption measurement revealed that the pore size of the mesoporous silica nanoparticles was about 2-3 nm (FIG. 3), with a surface area of 858 m$^2$/g. The accessible thiol groups on the mesoporous silica nanoparticles were quantified with Ellman's reagent using cysteine as a reference standard. The amount of thiol groups was 31 µmol/g.

Figure 4:
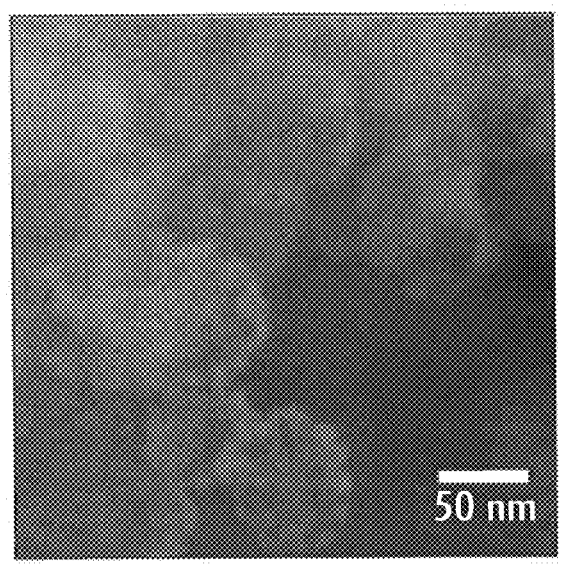
FIG. 4 presents an SEM image of hybrid nanoparticles. The image was acquired with a Zeiss Ultra Plus FESEM at the magnification of 300,000×.
Figure 5A:
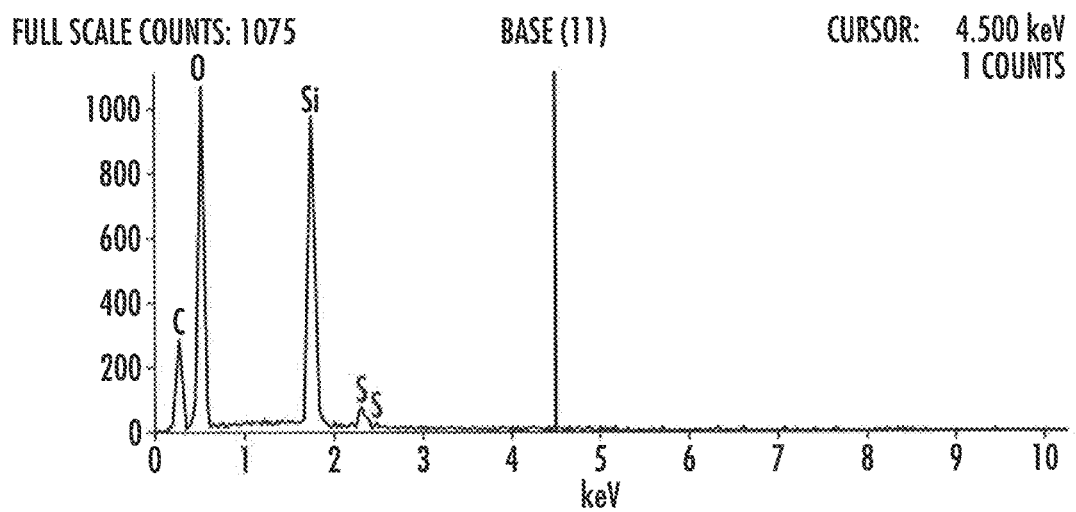
FIG. 5A presents SEM-EDX analysis of thiol functionalized mesoporous silica nanoparticles MSN-SH.
Figure 5B:
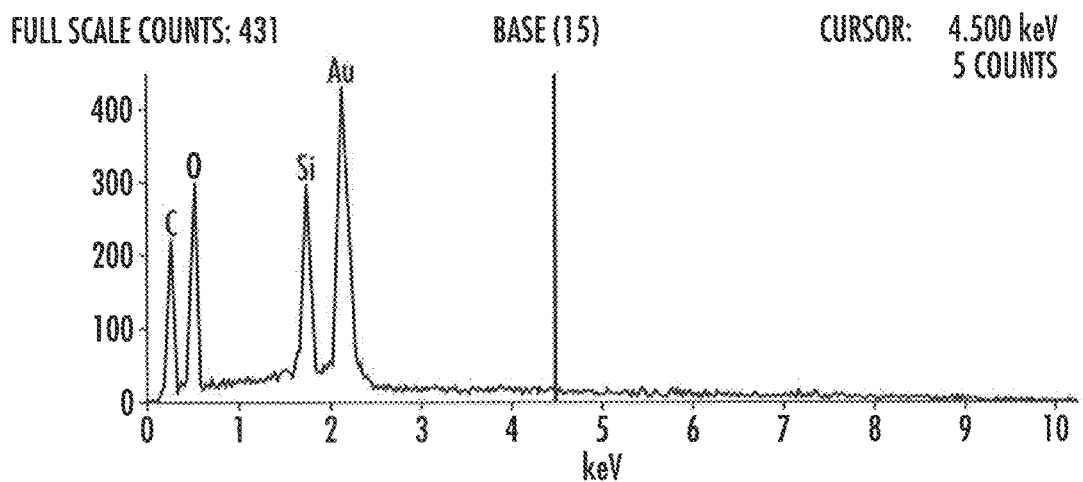
FIG. 5B presents SEM-EDX analysis of the formed hybrid nanoparticles.
Figure 6:
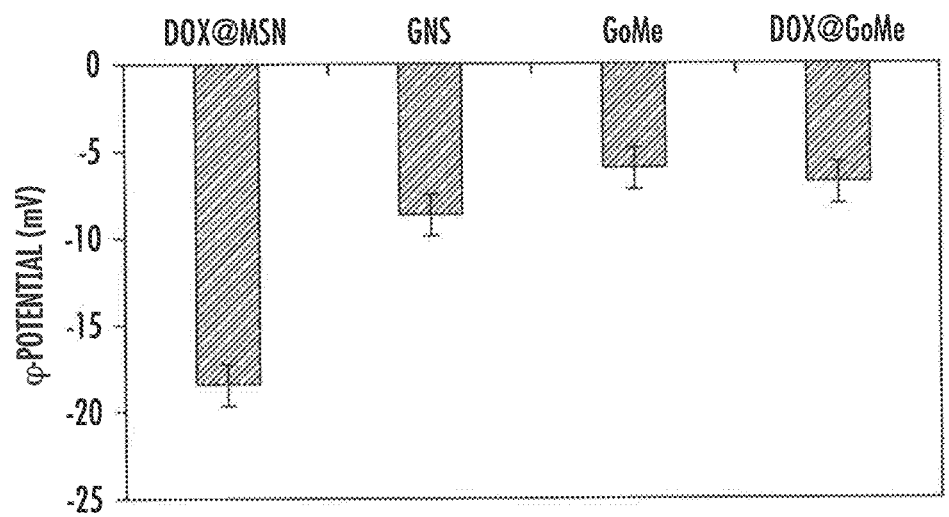
FIG. 6 presents the surface charge of mesoporous silica nanoparticles, gold nanospheres, hybrid nanoparticles, and hybrid nanoparticles loaded with doxorubicin DOX@GoMe.
Figure 7:
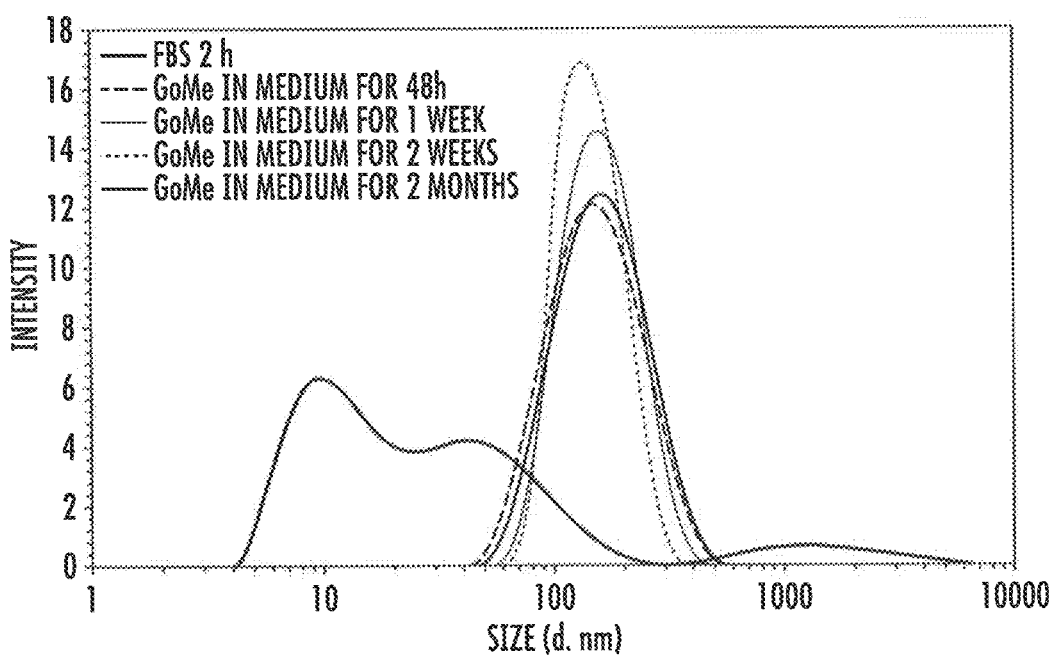
FIG. 7 presents the size distribution of hybrid nanoparticles in DI water and cell culture medium supplemented with 10% FBS.

The PEG-GNS were spherical with a diameter of 3.93±0.70 nm. The PEG-GNS were further functionalized as described to yield PDA-GNS. DTNB assay revealed that about 200 PDA molecules were anchored to each gold nanosphere. PDA-GNS was grafted onto MSN as described. TEM was employed to investigate the assembly between the gold nanospheres and the mesoporous silica nanoparticles. FIG. 4 showed that most gold nanospheres were evenly attached to the surface of the mesoporous silica nanoparticles. Surprisingly, only a few free gold nanospheres were detected after the reaction, indicating the high efficiency of the conjugation reaction. The success of grafting of gold nanospheres onto mesoporous silica nanoparticles was further confirmed by SEM image and SEM/EDX analysis. The evenly distributed small spherical dots on the bigger nanoparticles (FIG. 4) and the presence of Au element (FIG. 5B) indicated that GoMe had a structure as shown in FIG. 1. Zetasizer found that GoMe carried slightly negative surface charge (−5.92±0.75 mV, FIG. 6). Due to the existence of the PEG outer layer, GoMe was stable in culture medium containing 10% FBS (FIG. 7), and no obvious size change and aggregation were observed after two months of incubation. The size of GoMe determined by dynamic light scattering (DLS, 141.7 nm) was larger than that observed by TEM (54.71±9.63 nm), which is because that TEM measures physical size of the dried particles while DLS measures their hydrodynamic diameter (including the water layer surrounding the particle).

Photothermal Property Characterization

Figure 8A:
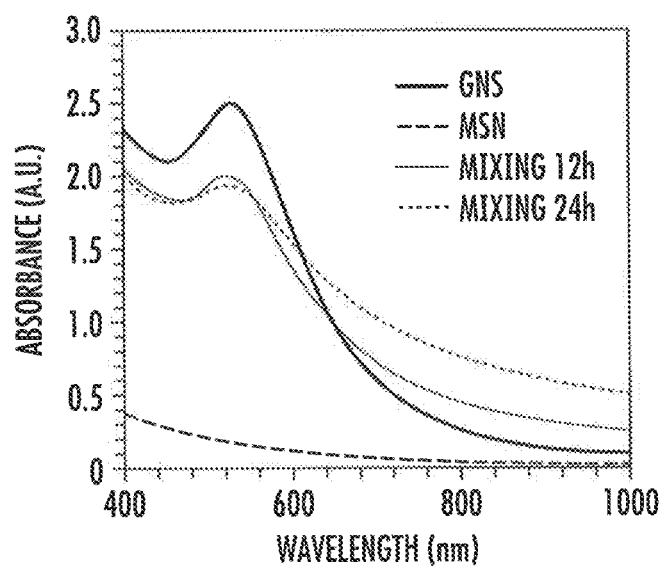
FIG. 8A presents the UV-Vis spectra of mesoporous silica nanoparticles, gold nanospheres, and their mixture after 12 and 24 h of reaction.
Figure 8B:
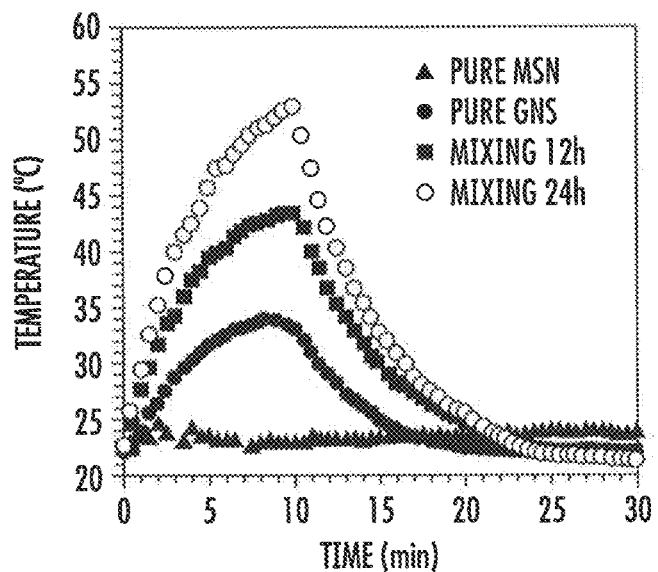
FIG. 8B presents the photothermal heating curves of mesoporous silica nanoparticles, gold nanospheres, and their mixture after 12 and 24 h of reaction upon 10 min of 808 nm laser irradiation (2.83 W/cm$^2$).

To monitor the fabrication progress of GoMe, UV-Vis spectrophotometer was employed by recording the absorbance from 400 to 1000 nm during the reaction. As shown in FIG. 8A, the absorbance peak of the reaction mixture at 524 nm decreased over time and slightly shifted to long wavelength direction, while its absorbance in the NIR region gradually increased. To evaluate the photothermal properties of the reaction mixture changing with the progress of the reaction, the reaction suspension was irradiated with NIR laser (808 nm, 2.83 W/cm$^2$) for 10 min at predesigned time intervals and its temperature was monitored with a FLIR i7 thermal imaging camera and recorded every 30 sec. Before the mixing, the aqueous nano-suspension of mesoporous silica nanoparticles produced none while the gold nanospheres produced little heat under the NIR irradiation (FIG. 8B). After 12 h of reaction, the temperature of the mixture of mesoporous silica nanoparticles and gold nanospheres raised 21.2° C. after irradiation (FIG. 8 B). Furthermore, the longer the reaction time, the higher the temperature reached. The mixture after 24 h of reaction could be heated to 52.8° C. (30° C. increase) upon the same intensity and length of NIR irradiation. The photothermal conversion efficiency of GoMe was 29.65%, which is slightly higher than the reported gold nanospheres (25%) while lower than gold nanorods (50%).

Figures 8C, 8D, 8E:
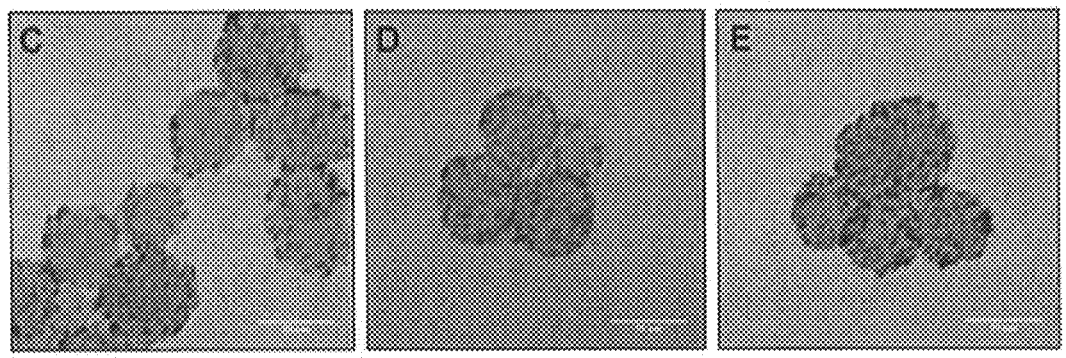
FIG. 8C presents TEM images of hybrid nanoparticles formed after 2 h of mixing mesoporous silica nanoparticles and gold nanospheres.
FIG. 8D presents TEM images of hybrid nanoparticles formed after 12 h of mixing mesoporous silica nanoparticles and gold nanospheres.
FIG. 8E presents TEM images of hybrid nanoparticles formed after 24 h of mixing mesoporous silica nanoparticles and gold nanospheres. Scale bars are 50 nm in FIG. 8C, FIG. 8D, and FIG. 8E.
Figure 9:
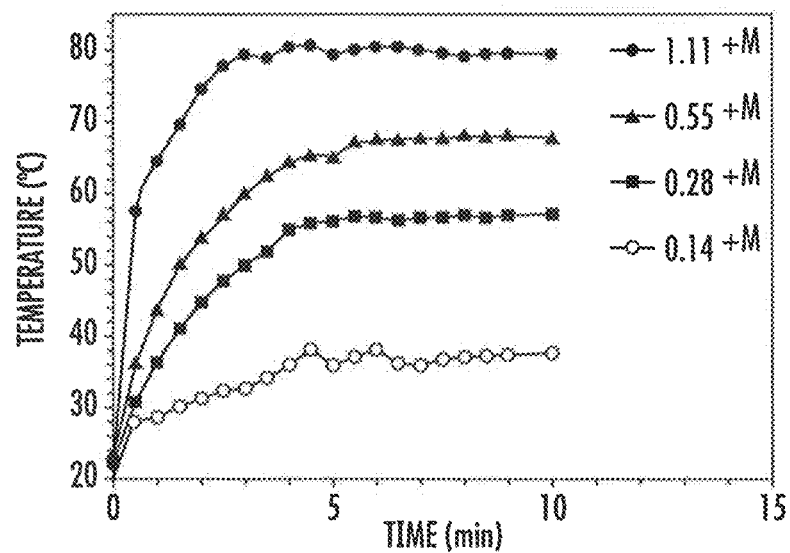
FIG. 9 presents the photothermal effect of hybrid nanoparticles at different concentrations (calculated based on gold nanospheres) at fixed gold nanosphere decorating density. A nano-suspension of the hybrid nanoparticles was irradiated by a 808 nm laser (2.83 W/cm$^2$).

To probe the mechanism for the mixture of gold nanospheres and mesoporous silica nanoparticles generating heat upon NIR laser irradiation, TEM was employed to observe the morphology change during the reaction. The reaction mixture was centrifuged to remove unconjugated gold nanospheres before loaded onto copper grids for TEM observation. FIG. 8C illustrates that gold nanospheres can be conjugated onto mesoporous silica nanoparticles within 2 h. Longer reaction time resulted in a higher gold nanospheres decorating density on the surface of the mesoporous silica nanoparticles (FIG. 8D and FIG. 8E). Altogether, higher decorating density of gold nanospheres on GoMe led to a higher absorbance in the NIR region, which opened the window for the biomedical application of GoMe using a NIR laser (FIG. 8A). As a consequence, GoMe with higher gold nanosphere decorating density produced more heat upon the NIR laser irradiation (FIG. 8B). FIG. 9 illustrates that GoMe exhibited a concentration-dependent photothermal heating effect. Therefore, a desired photothermal heating curve can be achieved by simply tuning the concentration of GoMe.

Figure 10:
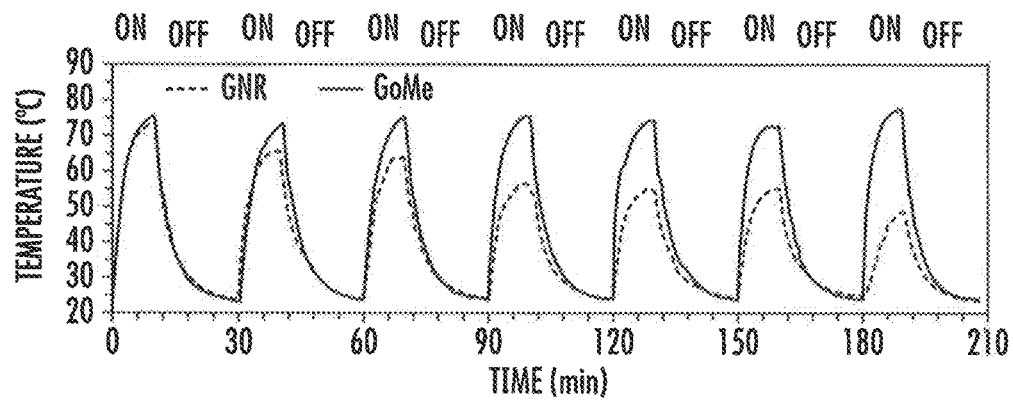
FIG. 10 presents real-time temperature elevation of hybrid nanoparticles and gold nanorod nano-suspensions during 7 cycles of NIR irradiation. Hybrid nanoparticles and gold nanorods were irradiated with a 808 nm NIR laser for 10 min (2.83 W/cm$^2$) and then cooled down for 20 min. The last cycle was carried out 24 h after the 6th cycle.

Photothermal stability is important for the success of photothermal therapy, especially when repetitive treatment is desired for the management of recurrent cancer. To evaluate the photothermal stability of GoMe, an aqueous suspension of GoMe was repetitively irradiated with an 808 nm NIR laser (10 min on and 20 min off) at the light intensity of 2.83 W/cm$^2$. The temperature of the nano-suspension was monitored as described above. Gold nanorods (aspect ratio of 3.89 and peak absorbance of 804 nm) synthesized according to the literature was employed as a control. Gold nanorods at a concentration that could produce heat to reach similar temperature as that of GoMe was irradiated in parallel. As illustrated in FIG. 10, the temperature of both GoMe and gold nanorod suspensions increased rapidly upon laser irradiation and reached 74° C. in 10 min. As expected, the repetitive heating of the gold nanorod suspension resulted in decreased peak temperatures, declining from 74° C. to 65.8° C. during the second heating cycle and further dropping to 48.5° C. after 6 cycles of laser irradiation induced heating/cooling. The GoMe suspension, on the other hand, reached the same peak temperature after 6 heating/cooling cycles, and achieved even higher peak temperature after 24 h of resting period, which suggests that GoMe was stable in keeping its photothermal property during laser irradiation induced heating/cooling process. Such stability is critical for certain biomedical applications which require multiple laser irradiations.

Figure 11:
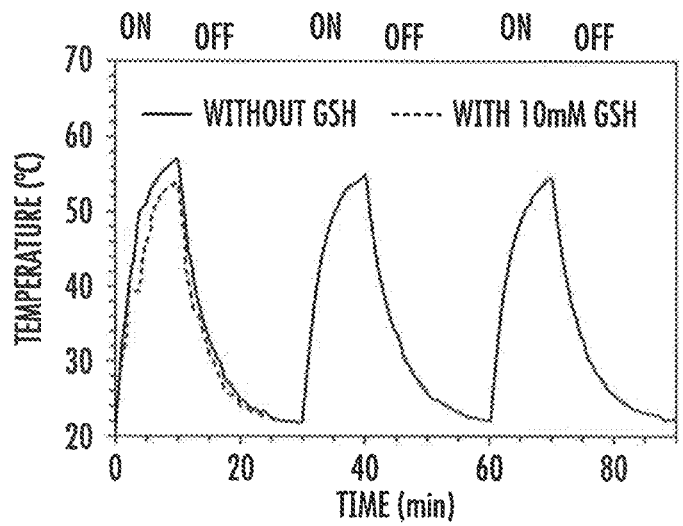
FIG. 11 presents the photothermal effect of hybrid nanoparticles in medium with or without 10 mM glutathione. A nano-suspension of the hybrid nanoparticles was irradiated by a 808 nm laser (2.83 W/cm$^2$, 10 min on and 20 min off).

Since gold nanospheres were grafted onto mesoporous silica nanoparticles through disulfide bonds, the photothermal property of GoMe in reducing environment was further investigated. FIG. 11 illustrates that the GoMe only slightly decreased its peak temperature in an environment containing 10 mM glutathione, suggesting that most of the gold nanospheres were still attached to the mesoporous silica nanoparticles. As it had been confirmed that each gold nanosphere had approximately 200 thiol reactive PDA groups, it is reasonable to postulate that every gold nanosphere was connected with a mesoporous silica nanoparticle through multiple disulfide bonds. Therefore, at any given time, glutathione only cleaved a part of those disulfide bonds of each gold nanosphere and merely loosened the binding between each gold nanosphere and the mesoporous silica nanoparticle. More importantly, repetitive heating/cooling in reducing environment did not change its photothermal converting capacity (FIG. 11), and the GoMe retained its competence in generating heat upon NIR irradiation in an intracellular environment, where it would encounter a relatively high glutathione level.

Figure 12A:
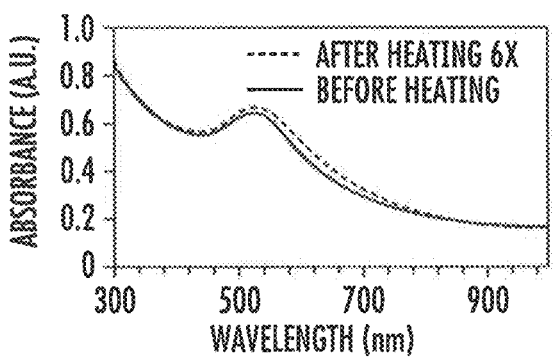
FIG. 12A presents the UV-Vis spectra of hybrid nanoparticles before laser irradiation and after 5 cycles of irradiation induced heating/cooling.
Figure 12B:
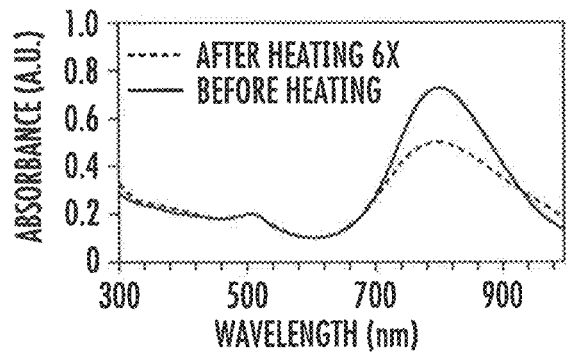
FIG. 12B presents the UV-Vis spectra of gold nanorods before laser irradiation and after 5 cycles of irradiation induced heating/cooling.
Figure 12C:
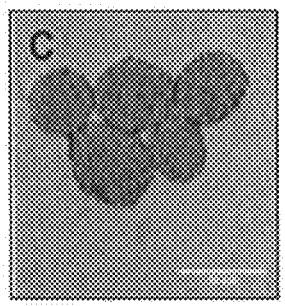
FIG. 12C presents TEM images of hybrid nanoparticles before laser irradiation.
Figure 12D:
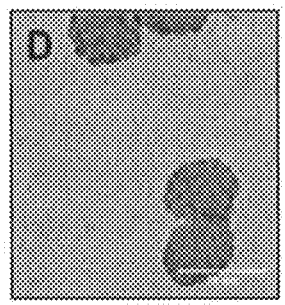
FIG. 12D presents TEM images of hybrid nanoparticles after 5 cycles of irradiation induced heating/cooling.
Figure 12E:
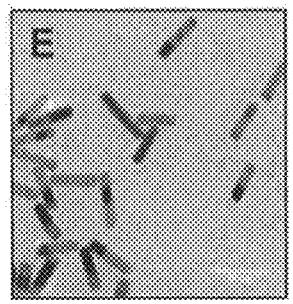
FIG. 12E presents TEM images of gold nanorods before laser irradiation.
Figure 12F:
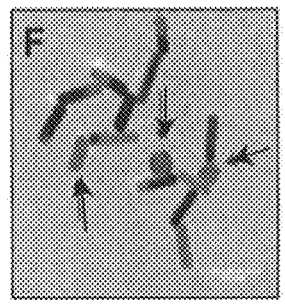
FIG. 12F presents TEM images of gold nanorods after 5 cycles of irradiation induced heating/cooling. Arrows indicate those gold nanorods changed to round shape. Scale bars in FIGS. 12C, 12D, 12E, and 12F are 50 nm.

To probe why GoMe was stable during the NIR laser irradiation induced heating/cooling cycles, while gold nanorod was instable, the UV-Vis spectra of GoMe and gold nanorod after each cycle were recorded. The UV-Vis absorbance of GoMe only marginally changed after 6 cycles of heating/cooling (FIG. 12A), while the absorbance of the gold nanorod suspension significantly diminished in the NIR region (FIG. 12B). To investigate the morphologies of the gold nanorod and GoMe after above treatment, TEM was employed. FIG. 12D illustrates that the morphology of GoMe remained intact after laser irradiation. By contrast, some gold nanorods changed their shape significantly after 5 cycles of laser irradiation, becoming shorter and fatter or round (FIG. 12F). This rod-to-sphere shape transformation was due to the melting of the gold nanorods under the extensive heat itself generated. Since gold nanoparticles melt at high temperature and form gold nano-droplet (or so called nanosphere), similar shape transformations also have be documented for gold nanoshells and gold nanocages. As a consequence of losing their original geometries, these gold nanoparticles showed a compromised photothermal property. However, GoMe, which was fabricated from gold nanospheres and mesoporous silica nanoparticles, kept its shape unchanged, since the gold nanospheres remain in the original spherical even after melting. Therefore, GoMe kept its photothermal capacity intact over multiple heating/cooling cycles.

Drug Release Kinetics Measurement

To investigate whether the decoration of gold nanospheres on the surface of mesoporous silica nanoparticles could affect the release profile of its payload, anticancer drug doxorubicin (DOX) was adopted as a model drug and loaded into the mesoporous silica nanoparticles as described. Due to its high surface area and pore volume, GoMe achieved 28% drug loaded content. Because DOX is a potent anti-cancer drug, DOX loaded GoMe (DOX@GoMe) of 4.58% drug loading content was adopted for the in vitro assay. However, in drug release kinetics study, the DOX@GoMe of 28% drug loading content was employed to achieve a more accurate drug release profile.

Figure 13A:
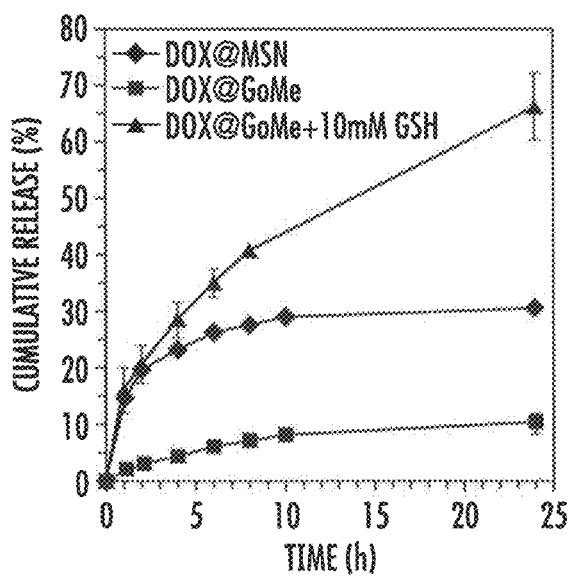
FIG. 13A presents the release kinetics of hybrid nanoparticles in plain PBS or PBS supplemented with glutathione.

An ideal drug carrier should be premature-release free before reaching its target. Furthermore, for a desired delivery system, the release of the payload should be either spontaneously responsive to the stimuli from its target or capable of being remotely controlled by external signals. To investigate the release kinetics of DOX from GoMe, DOX@GoMe was suspended in phosphate buffer (PBS, pH 7.4) and PBS supplemented with 10 mM glutathione to mimic the environments in the circulating blood and cytosol, respectively. Researchers have previously found that surface non-modified MSN can easily aggregate in aqueous medium, which could result in false release profile. Thus, for comparison, DOX loaded MSN (DOX@MSN) was also stabilized though PEG-SH surface modification. As shown in FIG. 13A, DOX@MSN released more than 28.8% of its payload within 10 h of incubation in PBS, suggesting that unsealed MSN was not a desired carrier. Interestingly, the hybrid nanoparticles, GoMe, released much less DOX (8.3%) within the same period of time, indicating that the gold nanospheres can serve as a plug to prevent DOX from leaking out from the pores of the mesoporous silica nanoparticles during circulating in blood stream.

Since gold nanospheres were conjugated onto the surface of the mesoporous silica nanoparticles through disulfide bonds, the responsiveness of GoMe to a reducing environment was further investigated by dispersing hybrid GoMe nanoparticles in PBS supplemented with 10 mM glutathione. As expected, GoMe released much more DOX in reducing environment (66.4% of DOX within 24 h) than that in PBS (10.3%), demonstrating that GoMe was a good carrier for intracellular drug delivery.

Figure 13B:
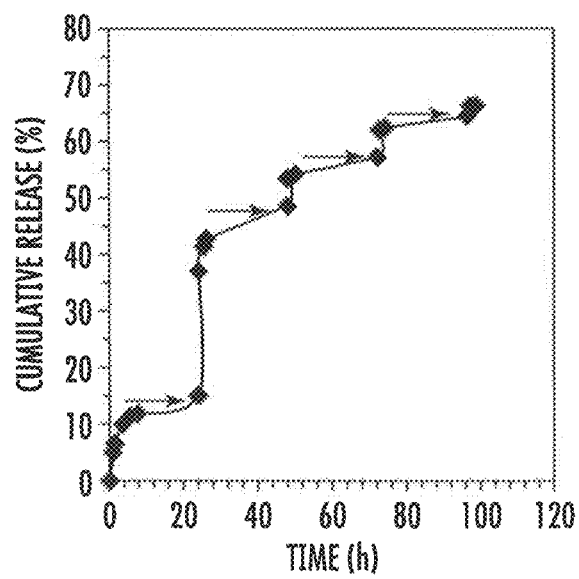
FIG. 13B presents the release kinetics of hybrid nanoparticles under the trigger of NIR irradiation. The arrows indicate the time points when the irradiation (10 min, 2.83 W/cm$^2$) was applied. Data are presented as mean±SD, n=3.

As discussed above, GoMe can efficiently convert NIR laser irradiation into heat. Thus, further investigation was carried out to examine the effect of NIR irradiation on drug release by applying irradiation (10 min laser on in every 24 h period) on the GoMe nano-suspension. As shown in FIG. 13B, 10 min of NIR irradiation induced more than 23% immediate DOX release. The removal of laser irradiation promptly slowed down the drug release. Moreover, the re-introducing of laser irradiation was shown to accelerate drug release repetitively. The first time NIR irradiation triggered more drug release than the later ones, which possibly due to the liberation of drugs bonded on the surface MSN for the first irradiation while later stimuli induced the release of encapsulated drugs from the pores of MSN. This light activable two-stage drug release pattern can be utilized to meet the clinical setting in drug administration by providing both loading dose and maintenance dose.

Observation of GoMe by Confocal Fluorescent and Dark-Field Microscopies

Figure 14:
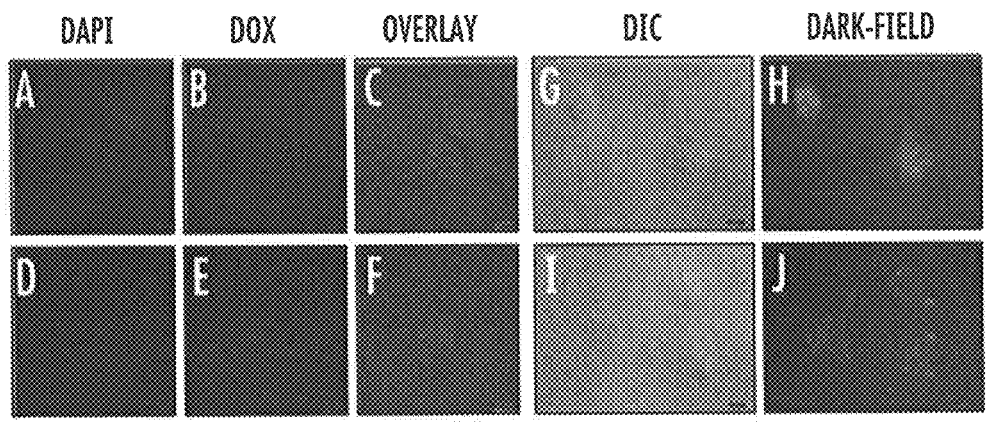
FIG. 14 illustrates the confocal (A-F) and dark-field (G-J) images of A2058 cells co-cultured with DOX@GoMe. Cells in A-C, and G-H were control. Cells in D-F, and I-J were treated with DOX@GoMe. Images H and J were collected in dark-field mode. Scale bars in A-J are 10 μm.

To explore the potential of using GoMe as a carrier to deliver drug into cancer cells, DOX-loaded GoMe was co-incubated with A2058 melanoma cells for 3 h, and then observed with a confocal microscope. The fluorescence signals in FIG. 14 at (F) show that GoMe loaded DOX effectively entered the A2058 cells. To further confirm that GoMe entered cancer cells, the above cells were also observed with a dark-field microscope. Scatter light signals collected inside A2058 cells (FIG. 14 at (J)) through a dark-field detector and demonstrated that the GoMe was taken up by cancer cells.

Cell Killing Effect of GoMe

Figure 15:
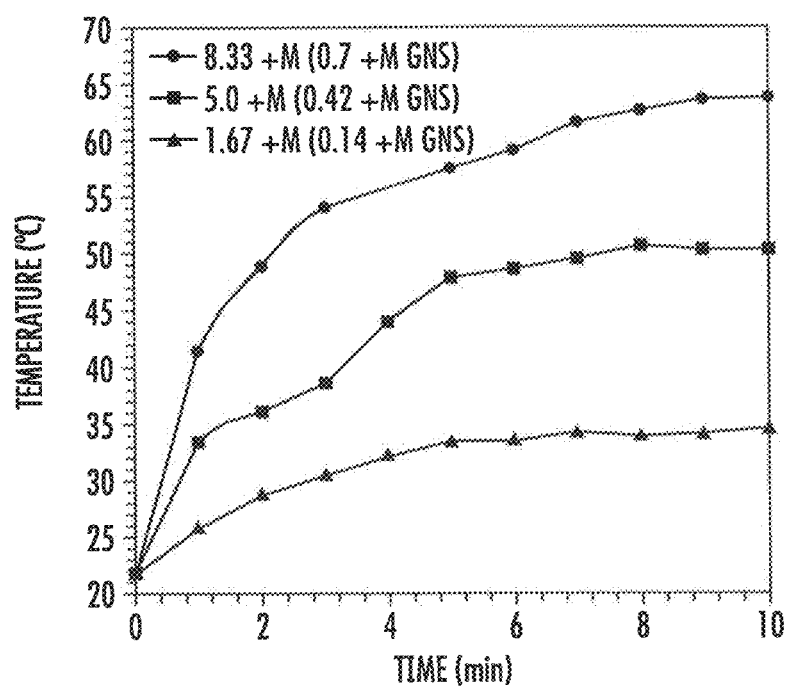
FIG. 15 presents the real-time medium temperature during NIR laser irradiation of different hybrid nanoparticle concentrations (calculated based on corresponding doxorubicin concentration).
Figures 16A, 16B, 16C:
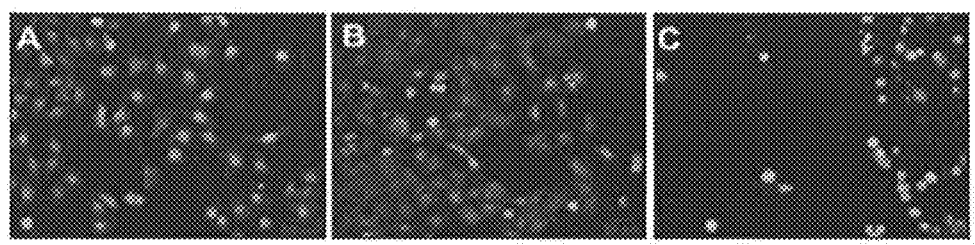
FIG. 16A presents fluorescent images of live/dead cell assay after NIR irradiation. Cells in FIG. 16A were treated with blank medium.
FIG. 16B presents fluorescent images of live/dead cell assay after NIR irradiation. Cells in FIG. 16B were treated with blank hybrid nanoparticles.
FIG. 16C presents fluorescent images of live/dead cell assay after NIR irradiation. Cells in FIG. 16C were treated with hybrid nanoparticles coupled with NIR irradiation. The laser dose was 10 min, 2.83 W/cm$^2$. Scale bars in FIGS. 16A, 16B, and 16C are 50 μm. Data were presented as mean±SD, n=3, P<0.05 *; P<0.01 #).

FIG. 15 illustrates that GoMe raised the median temperature from 21.8° C. to 34.6° C. and 50.3° C. within 10 min of laser irradiation at GoMe concentrations corresponding to 1.67 µM and 5 µM DOX, respectively. Since GoMe can generate heat and raise median temperature upon NIR laser irradiation, the photothermal therapy effect on the cancer cells was investigated through Live/Dead cell assay. A2058 cells were co-incubated with blank GoMe at the corresponding DOX concentration of 5 µM and coupled with NIR laser irradiated for 10 min before the Live/Dead cell assay, and then visualized with a fluorescent microscope. As expected, nearly all non-treated cells were stretched and green (FIG. 16A). It was also noted that blank GoMe treated cells (FIG. 16B) did not show any morphology difference as compared with the non-treated ones, suggesting GoMe itself was not toxic. By contrast, cells treated with blank GoMe and laser irradiation dramatically changed their morphology, showing round shape (FIG. 16C). It was also noticed in FIG. 16C that the cell density was much lower than the group that did not receive laser irradiation, which was due to the detaching of cells as a result of apoptosis and subsequently being removed during the washing procedure. In addition as shown in FIG. 16C, a significant portion of cells were stained in red, confirming that GoMe coupled with NIR irradiation effectively killed cancer cells.

Figure 16D:
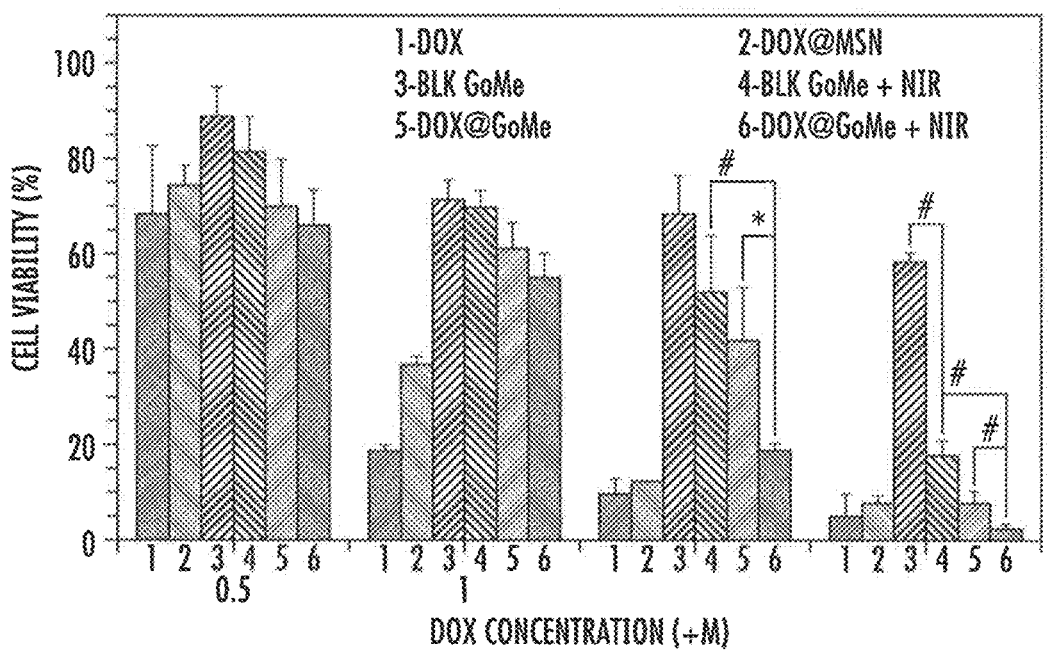
FIG. 16D presents cytotoxicity of DOX@GoMe coupled with NIR irradiation.

It was confirmed that NIR laser irradiation can trigger the release of DOX from GoMe and that photothermal effect of blank GoMe can kill cancer cells. To investigate the cell killing efficacy of DOX@GoMe coupled with NIR irradiation, A2058 cells receiving different treatments were analyzed by MTT assay. Due to the potential residual of cetyl trimethylammonium bromide (CTAB) in the mesoporous silica nanoparticles, blank GoMe showed some cytotoxicity. As expected, the application of NIR irradiation enhanced the cell killing effect of GoMe (FIG. 16D), especially for GoMe at the concentration of 5 µM. Because the capping effect of gold nanospheres and the consequent slower drug release, DOX@GoMe was less potent than DOX@MSN in killing cancer cells. Furthermore, FIG. 16D also illustrates that the DOX@GoMe coupled with NIR irradiation did show superior anticancer efficacy than either GoMe coupled with NIR irradiation or DOX@GoMe alone. Due to the photothermal effect of GoMe, NIR irradiation of DOX@GoMe can kill cancer cells by the combination effect of photothermal ablation and boosted drug release and subsequent enhanced chemotherapy. It is worth noting that the effect of NIR irradiation became significant when GoMe concentration reached 2 µM, at which GoMe can generate enough heat to ablate cancer cells and augment drug release. The combination index (CI) analysis further revealed that the combination of DOX@GoMe and NIR irradiation exhibited synergistic effect at the DOX concentration 5 µM (CI value=0.50). Therefore, high retention of DOX@GoMe in the targeted tissue or cells can lead to the synergistic effect between DOX@GoMe and NIR irradiation.

In Vivo Tumor Detection

Figures 17A, 17B:
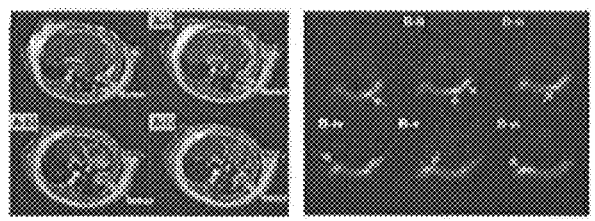
FIG. 17A presents four contiguous MRI transverse images of 3 tumors in the lung of a mouse that received radiolabeled hybrid nanoparticles. Tumors are indicated by arrows in FIG. 17A.
FIG. 17B provides PET images of contiguous slices of the 3 tumors in the lung of a mouse that received radiolabeled hybrid nanoparticles. The images were acquired 6 h post-administration.
Figures 17C, 17D:
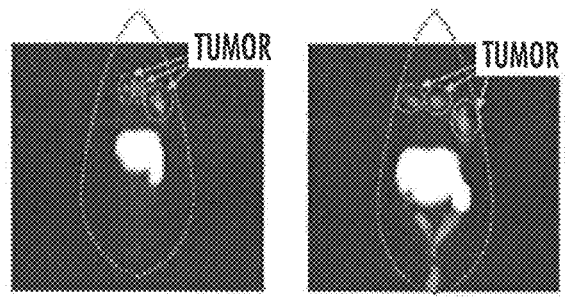
FIG. 17C provides a whole body PET image of the mouse acquired 6 h post-administration.
FIG. 17D provides a whole body PET images of the mouse acquired 20 h post-administration.

To endow the PET imaging function to GoMe, DOTA was conjugated onto GoMe nanoparticles by adding maleimido-mono-amide-DOTA. With the help of conjugated DOTA, the yield for GoMe $^{64}$Cu-labeling was above 98%, which suggests that GoMe is a good carrier for radiopharmaceuticals. To validate that $^{64}$Cu-labeled GoMe can be used as a tool for cancer detection, a clinically relevant spontaneous lung tumor model was employed. The 3 small tumors in the lung (previously revealed by a ClinScan MRI system as shown in FIG. 17A were clearly detected by PET at both 6 h (FIG. 17B, FIG. 17C) and 20 h (FIG. 17D) post-administration, suggesting the high retention of GoMe in the tumor, which proved that GoMe is good tool for cancer detection. Similar to other nanoparticles, significant amount of GoMe nanoparticles accumulated in liver and spleen as shown in the PET images. The increase of PET signals in the abdomen (colon and rectum) from 6 h to 20 h revealed the route that the GoMe was cleared from the body.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A hybrid nanoparticle comprising a mesoporous silica nanoparticle and a plurality of gold nanospheres bonded to the mesoporous silica nanoparticle, wherein each gold nanosphere is bonded to the mesoporous silica nanoparticle by a plurality of disulfide bonds, and wherein the mesoporous silica nanoparticle includes a plurality of pores loaded with an active agent, and wherein the plurality of pores have a pore size of about 2 to about 3 nm, and wherein of the plurality of gold nanospheres have a diameter of about 5 to about 40 nm, and wherein the active agent comprises a photosensitizer, and wherein release of the active agent can be triggered by exposing the hybrid nanoparticle to near infrared (NIR) radiation as well as by exposing the hybrid nanoparticle to a decrease in redox potential and wherein exposing the hybrid nanoparticle to NIR irradiation can produce a cytotoxic photothermal temperature increase.

2. The hybrid nanoparticle of claim 1, wherein the active agent further comprises a drug.

3. The hybrid nanoparticle of claim 2, wherein the drug is a chemotherapy drug.

4. The hybrid nanoparticle of claim 1, further comprising a detectable substance bonded to the hybrid nanoparticle.

5. The hybrid nanoparticle of claim 1, further comprising a targeting ligand bonded to the hybrid nanoparticle.

6. The hybrid nanoparticle of claim 1, further comprising pyridine groups on the hybrid nanoparticles.

7. The hybrid nanoparticle of claim 1, further comprising polyethylene glycol on the hybrid nanoparticle.

8. A method for forming the hybrid nanoparticle of claim 1 comprising:
    functionalizing a mesoporous silica nanoparticle with a first thiol reactivity;
    functionalizing a plurality of gold nanospheres with a second thiol reactivity;
    reacting the first reactivity with the second reactivity such that the plurality of gold nanospheres are bonded to a surface of the mesoporous silica nanoparticle via a plurality of disulfide bonds; and
    loading the mesoporous silica nanoparticle with the active agent, thereby forming the hybrid nanoparticle of claim 1.

9. The method of claim 8, wherein the active agent comprises a drug and the photosensitizer.

10. The method of claim 9, wherein the drug comprises a chemotherapy drug.

11. The method of claim 8, further comprising bonding a detectable substance to the hybrid nanoparticle.

12. The method of claim 8, further comprising bonding a targeting ligand to the hybrid nanoparticle.

13. A method for photothermally treating a living cell comprising:
    locating the hybrid nanoparticle of claim 1 in an environment, the environment comprising a living cell;
    directing electromagnetic radiation at the hybrid nanoparticle in the environment such that the temperature in the environment increases due to the electromagnetic radiation interacting with the hybrid nanoparticle, the electromagnetic radiation comprising light having a wavelength of from 650 nanometers to 900 nanometers.

14. The method of claim 13, further comprising releasing a drug from the hybrid nanoparticle in the environment.

15. The method of claim 14, wherein the rate of release of the drug from the hybrid nanoparticle is controlled by the electromagnetic radiation.

16. The method of claim 13, the hybrid nanoparticle further comprising a binding ligand, the method further comprising binding the hybrid nanoparticle to the living cell via the binding ligand.

17. The method of claim 13, the hybrid nanoparticle further comprising a detectable agent, the method further comprising detecting the hybrid nanoparticle in the environment via the detectable agent.

18. The method of claim 17, wherein the hybrid nanoparticle is detected according to a positron emission tomography process.

19. The method of claim 13, further comprising allowing the temperature in the environment to decrease and repeating the process one or more times, the hybrid nanoparticle retaining one or more photothermal characteristics following the repetition of the process.

* * * * *